United States Patent
Ma (10) Patent No.: US 8,553,831 B2
(45) Date of Patent: Oct. 8, 2013

(54) IMAGING SYSTEM AND METHOD USING PRIMARY AND SCATTERED RADIATIONS

(76) Inventor: Feng Ma, Cary, NC (US)

( * ) Notice: Subject to any disclaimer, the term of this patent is extended or adjusted under 35 U.S.C. 154(b) by 0 days.

(21) Appl. No.: 13/565,819

(22) Filed: Aug. 3, 2012

(65) Prior Publication Data

US 2012/0294413 A1 Nov. 22, 2012

Related U.S. Application Data

(63) Continuation of application No. 12/067,383, filed as application No. PCT/US2006/036550 on Sep. 19, 2006, now Pat. No. 8,238,513.

(60) Provisional application No. 60/596,348, filed on Sep. 19, 2005.

(51) Int. Cl.
*A61B 6/00* (2006.01)

(52) U.S. Cl.
USPC .............................................. 378/6; 382/131

(58) Field of Classification Search
USPC .............................................. 378/6; 382/131
See application file for complete search history.

(56) References Cited

U.S. PATENT DOCUMENTS

| | | | | | |
|---|---|---|---|---|---|
| 4,375,695 | A | * | 3/1983 | Harding et al. | 378/6 |
| 4,656,650 | A | * | 4/1987 | Kikuchi et al. | 378/7 |
| 4,823,370 | A | * | 4/1989 | Kikuchi | 378/98.4 |
| 5,602,895 | A | * | 2/1997 | Fivez et al. | 378/98.4 |
| 6,163,589 | A | * | 12/2000 | Vartanian | 378/7 |
| 6,272,198 | B1 | * | 8/2001 | Shimura | 378/7 |

* cited by examiner

*Primary Examiner* — Alexander H Taningco (57) ABSTRACT

An imaging system and method configured to construct an image of an internal structure of an object. The imaging system including: a radiation source configured to generate both a narrow beam and a wide beam of radiation; a detector configured to detect the radiation; and at least one processing circuit configured to: determine a scatter-to-primary ratio (SPR) of the wide beam based on the narrow beam; determine a primary component of the wide beam based on the SPR to thereby separate the primary component from a scattered component of the wide beam; and construct the image using the primary component.

20 Claims, 6 Drawing Sheets

IMAGING SYSTEM AND METHOD USING PRIMARY AND SCATTERED RADIATIONS

CROSS-REFERENCE TO RELATED APPLICATIONS

The present application is a continuation of U.S. patent application Ser. No. 12/067,383 (now U.S. Pat. No. 8,238,513), filed Mar. 19, 2008, which is a national stage of PCT/US2006/036550, filed Sep. 19, 2006, which claims priority to U.S. Provisional Application No. 60/596,348, filed Sep. 19, 2005. The disclosures of these applications are hereby incorporated by reference in their entirety.

BACKGROUND

Radiations, such as X-ray, gamma rays, infrared and visible light, as well as mechanical waves such as sonic and ultrasonic waves have been used to probe internal structures of an object. Radiography, mammographic imaging, ultrasound, Computed Tomography (CT), Positron Emitting Tomography (PET), and Magnetic Resonance Imaging (MRI) have been used widely for medical diagnostic purposes, in industrial measurements, security checks, and other areas.

SUMMARY

In an aspect, a computed tomography (CT) imaging system is configured to construct an image of an internal structure of an object, the imaging system including: a radiation source configured to generate both a narrow beam and a wide beam of radiation; a detector configured to detect the radiation; and at least one processing circuit configured to: determine a scatter-to-primary ratio (SPR) of the wide beam based on the narrow beam; determine a primary component of the wide beam based on the SPR to thereby separate the primary component from a scattered component of the wide beam; and construct the image using the primary component.

In some implementations, the radiation source comprises a blocking device configured to generate both the narrow beam and the wide beam.

In some implementations, the detector is configured to move along the direction of the narrow beam to thereby measure a radiation level at a plurality of positions along the direction to facilitate the determining of the SPR.

In some implementations, the detector includes a plurality of detection elements disposed at a plurality of positions along the direction to facilitate the determining of the SPR.

In some implementations, the system includes a timing device configured to coordinate an emitting time from the radiation source and a detecting time of a detecting element of the detector, to thereby separate the primary component and the scattered component of the wide beam.

In some implementations, the at least one processing circuit is configured to use an analytical pencil beam model, and predict the primary component of the wide-beam X-ray radiation using the narrow beam based on the analytical pencil beam model.

In some implementations, the at least one processing circuit is configured to use a Monte Carlo algorithm, and predict the primary component of the wide-beam X-ray radiation.

In some implementations, the at least one processing circuit is configured to perform an iteration of an output image, wherein the output image is used as an input density map to the Monte Carlo algorithm, to generate more a accurate density map image.

In some implementations, the system further includes a timing device configured to turn on a detecting element for a short period such that the detecting element detects only the primary component.

In some implementations, the detector is configured to selectively read an output from a selected detecting element to thereby separate the primary and scattered components.

In some implementations, the at least one processing circuit is configured to generate an image of the internal structure based on the scattered component.

In another aspect, an image reconstruction method for Computed Tomography (CT) is provided, the method including: determining a scatter-to-primary ratio (SPR) of a wide beam based on a narrow beam; determining a primary component of the wide beam based on the SPR to thereby separate the primary component from a scattered component of the wide beam; and constructing an image of an internal structure of an object using the primary component.

In some implementations, the method further includes: using a first set of CT images without separating the primary and scattered components as input density maps to a computer model; constructing a second set of CT images based on the primary component using the computer model; and iterating the above operations to obtain CT images with improved accuracy.

In some implementations, the computer model comprises at least one of an analytical equation of an SPR as a function of a position and attenuation properties of a material along a beam path, or a Monte Carlo algorithm.

In some implementations, further comprising coordinating an emitting time from a radiation source and a detecting time of a detecting element, to facilitate separation of the primary component and the scattered component of the wide beam.

In some implementations, the method further includes turning on a detecting element for a short period such that the detecting element detects substantially only the primary component.

In some implementations, the method further includes selectively reading an output from a selected detecting element to thereby separate the primary and scattered components.

In another aspect, a non-transitory computer-readable medium is provided having instructions stored thereon, the instructions including: transmitting a narrow beam of radiation through an object onto a detector array; transmitting a wide beam of radiation through the object onto the detector array; recording radiation levels at a plurality of positions along a direction of the narrow beam using the detector array; calculating a scatter-to-primary ratio (SPR), using a computer model, as a function of position; separating primary and scattered components of the wide beam based on the calculated SPR; constructing a first set of CT images using the primary component; and constructing a second set of CT images using the scattered component.

In some implementations, the computer model includes an analytically-derived formula describing the SPR as a function of positions and attenuation properties of material along the direction of the narrow beam.

In some implementations, the computer model comprises a Monte-Carlo-derived numerical relation describing the SPR as a function of positions and attenuation properties of material along the direction of the narrow beam.

DETAILED DESCRIPTION

Various embodiments are described in detail below with reference to the drawings. Like reference numbers may be used to denote like parts throughout the figures.

When a beam of radiation or wave interacts with an internal structure of an object, a portion of the beam may be absorbed, and a portion may be scattered. The un-scattered portion of the beam, e.g., the primary radiation, traces more accurately the attenuation coefficient of the internal structure as compared with the scattered radiation.

Earlier generations of Computed Tomography (CT) use narrow beams or fan beams of X-rays, which suffer little from effects of scattered x-ray photons. Newer generations of CT systems use cone-beam x-rays, with a field size in the order of, for example, 10 cm. Flat-panel detector arrays may be used to reconstruct an attenuation map of an object (e.g., a patient). Such a setup may have advantages over traditional CTs that utilize narrow-beams or fan-beams. For example, the cone-beam CT may be faster and may achieve a more uniform resolution in a 3-D space.

However, as a result of the wide field at the target, cone-beamed x-ray beams may be associated with a large amount of scattered radiations that tend to blur the reconstructed images, wherein the images may be reconstructed based on the radiations absorbed by the detectors. In a low-energy range (~100 keV) of x-ray photons involved in diagnostic imaging, a scatter-to-primary ratio (SPR) may be on the order of 1, as compared to megavoltage x-rays, wherein typical SPR may be on the order of 0.1 or smaller.

It has been shown in measurements that scattered radiations may degrade the contrast-to-noise ratio (CNR) by a factor of 2 in a cone-beam CT. There may also be shading artifacts caused by scattered radiations. However, the benefits of volumetric (e.g., cone-beam) imaging warrant the effort to reduce scatter rather than going back to 2-D (fan-beam) or 1-D (pencil beam) imaging.

Swindell and Evans (Med. Phys., vol. 23, p. 63, 1996) have computed that the central axis SPR is almost linear with the beam area, and is also almost linear with depth in water for a 6 MV beam.

Bjarngard and Petti (Phys. Med. Biol. Vol. 33, p. 21, 1988) discovered that SPR(r,d), as a function of radius r and depth d, is a linear function of z:

$$SPR(r,d)=K\mu z, \quad (1)$$

where $\mu$ is the linear attenuation coefficient for primary photons, and $z=rd/(r+d)$, and K is a coefficient that may depend on the attenuation coefficient $\mu$. Nizin (Med. Phys. Vol. 18, p. 153) has used Eq. (1) to separate primary and scattered radiations in the case of a Co-60 beam in water.

Reducing "contaminations" from scattered radiations may be achieved using grids in front of detectors. In an article "The Influence of Antiscatter Grids on Soft-Tissue Detectability in Cone-Beam Computed Tomography with Flat-panel Detectors" by Siewerdsen et al. (Med. Phys., vol. 31, p. 3506, 2004), it was demonstrated that the grids may filter out a portion of the scattered radiation.

However, the usefulness of the grids may be based on an assumption that most of the scattered photons are in directions different from those of primary photons. Similar methods of separating scattered radiation from primary radiation may have been attempted over a thousand year ago. That is, separating primary from scattered radiations using grids in front of detectors may be analogous to the attempt of viewing stars through a long tube during daytime. While some limited success has been achieved using this approach, its limitation is obvious in that the scattered day (solar) light usually still dominates the primary (direct) light from the stars even in that narrow cone.

Endo et al. (Med. Phys. Vol. 28, p. 469, 2001) studied the effect of scattered radiations on image noise in cone-beam CT, and the effectiveness of a focused collimator or a grid in reducing the noise.

Separating primary and scatter radiation in CT imaging may also improve the usefulness of information conveyed by scattered photons in an x-ray inspection system (Mario, Arthur W. et al., U.S. Patent Application Pub. No. 20050089140, "Tomographic scanning x-ray inspection system using transmitted and Compton scattered radiation").

Mathematical models of separating primary and scattered radiations may have been explored in the field of megavoltage x-ray radiation therapy as an approach to research the different properties and behaviors of the primary component and the scattered component (e.g., P. S. Nizin, "Electronic equilibrium and primary dose in collimated photon beams", Med. Phys., 20, 1721-1729 (1993); P. S. Nizin, "Geometrical aspects of scatter-to-primary ratio and primary dose", Med. Phys., vol. 18, p. 153, 1991). However, in the field of radiation therapy, such approaches are merely research tools to improve the understanding of the physical process in an object, and may not be applied to linear accelerators to physically separate the primary and the scatter components.

Figure 1:
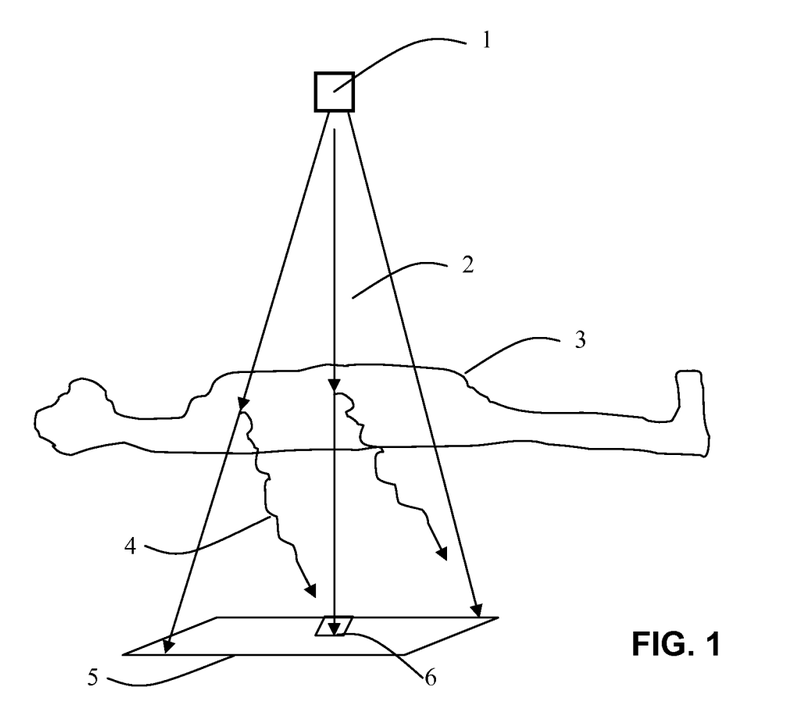
FIG. 1 is a schematic diagram illustrating an effect of scattered radiation in CT imaging.

FIG. 1 illustrates an example CT system. X-ray source 1 may emit a primary radiation beam 2, which may pass through an object (such as a patient) 3. Attenuation and scattering may be associated with the radiation passing through at least a portion of the object. Scattered radiation 4, traveling in the same direction or in a direction different from that of the primary radiation, may also reach the flat panel detector array 5. A detector element 6 may receive both the attenuated primary radiation and the scattered radiation.

Figure 2:
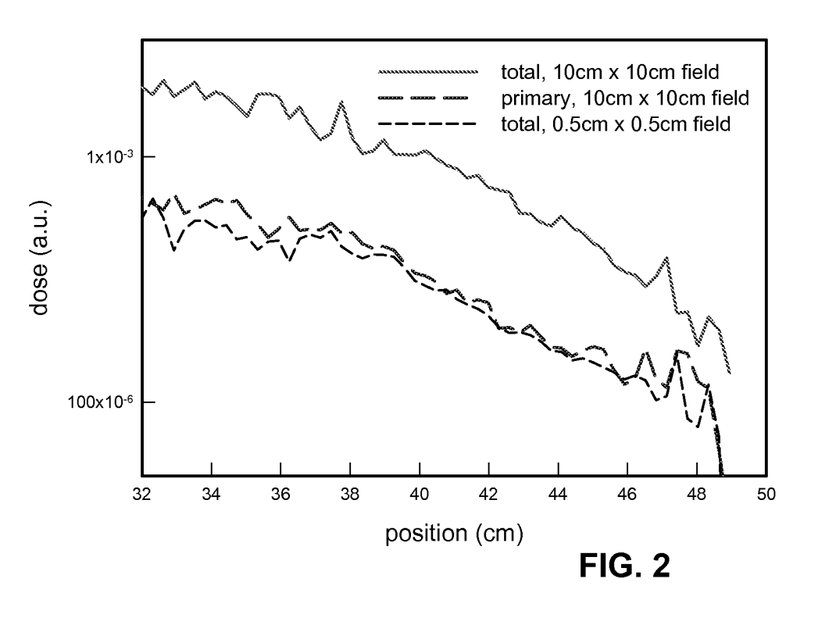
FIG. 2 is a plot illustrating that a total dose for a 0.5 cm, 140 keV X-ray beam in an object follows closely the primary dose of a 10 cm, 140 keV X-ray beam in the same object toward the same direction.

FIG. 2 illustrates Monte Carlo simulation results using methods of the disclosed implementations. Doses vs. depth in a patient are shown for 140 kV x-ray beams through an object. The total dose of a narrow (0.5 cm×0.5 cm) beam may follow closely of the primary dose of a cone beam (10 cm×10 cm at a position of 40 cm inside the patient). As such, the primary radiation of a cone beam may be simulated using a narrow beam according to embodiments disclosed herein. A simulation of a fan beam may produce similar results, i.e., the scattered radiation in a fan beam may also be very small.

Figure 3:
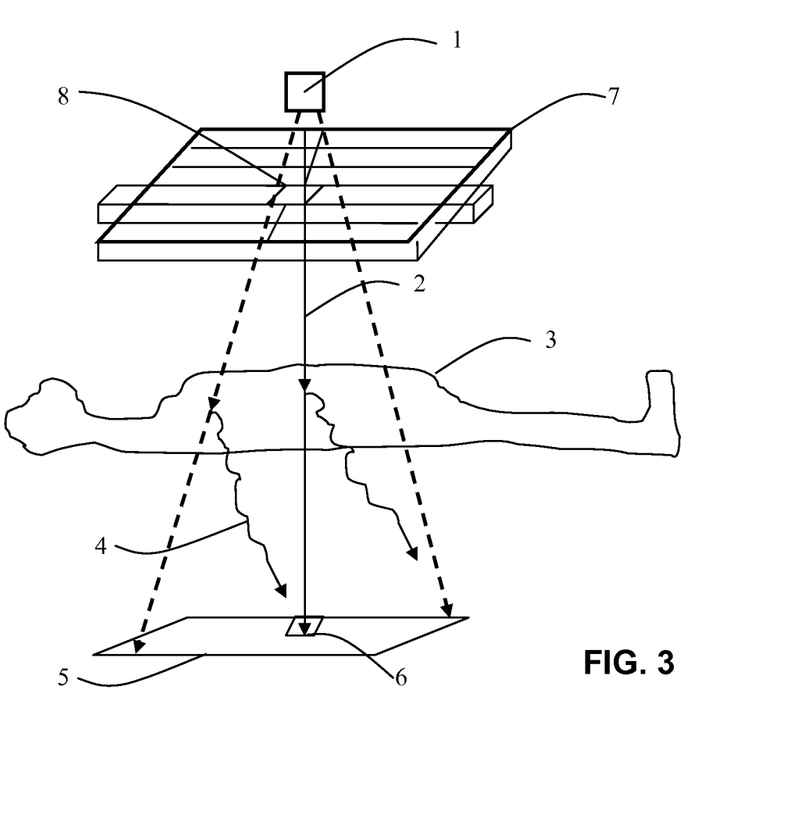
FIG. 3 is a schematic diagram illustrating an example configuration of a CT system utilizing a pencil beam (or a fan beam) and a cone beam.

Based on the results illustrated in FIG. 2, in accordance with some of the disclosed embodiments, a multi-leaf collimator 7 may be placed in front of the x-ray source 1 as illustrated FIG. 3. The collimator 7 may have a variable opening 8, which may be a small squared hole, a slit, or have any other shapes. The opening 8 may be smaller than the cone-beam itself.

In accordance with some embodiments, narrow (e.g., with a lateral span or diameter of 0.5 cm or smaller) x-ray beams may be obtained using the above-mentioned collimator, and may serve as probes to determine or predict the primary component in the cone beam.

According to some of the disclosed implementations, a detector recording a dose in the direction of the cone beam may send the measured dose information to a computer. The computer can calculate the primary dose, based on the measured dose and the knowledge obtained from the narrow beams.

The time and exposure spent on the small beams is not necessarily wasted, nor is the patient exposed more x-ray radiation without the advantages of an improved image. In some of the disclosed implementations, signals from the narrow beams and the cone beams may be combined, and the final signal-to-noise ratio (SNR) may still be proportional to the total radiation exposure, including the radiation exposures from both the narrow beams and the cone beam.

Blocking devices other than the multi-leaf collimator may be used to obtain the narrow and wide beams. For example, wedges, metal blocks, or radiation source shutters may be used as part of a blocking device. The narrow beam may be a pencil beam or a fan beam, or may have other shapes.

In some implementations, detector elements other than the detector element 6 may also be turned "on" to read the scattered radiations. The scattered radiations may then be used to predict the strength of the scattering. Such information may be input to an image reconstruction algorithm according to some of the disclosed embodiments.

In some implementations, a slit may be used instead of the small hole. The slit may effectively produce a fan beam, the dose of which may be used to separate the primary and scattered radiations of the cone beam. All the signals recorded by the detectors may be combined to avoid wasting the radiation (exposure to the patient) or time.

In some implementations, a combination of narrow beam (e.g., fan-beam) CT and wide beam (e.g., cone-beam) CT technologies may be employed. For example, during CT scans, an object (e.g., patient) may be exposed first to narrow (e.g., fan) beams, and then to wide (e.g., cone) beams. Alternatively, the object may be exposed first to wide beams, and then to fan beam.

The signals read off the detectors during the wide beam exposures may be associated with the total dose at the detectors. Such a total dose may be separated into primary and scatter components based on detector readout obtained from the narrow-beam exposures. The signals may be combined, and the primary dose may be used to reconstruct a first set of CT images, and the dose from the scattered radiation may be used to reconstruct a separate set of CT images corresponding to scattered radiation.

Figure 4:
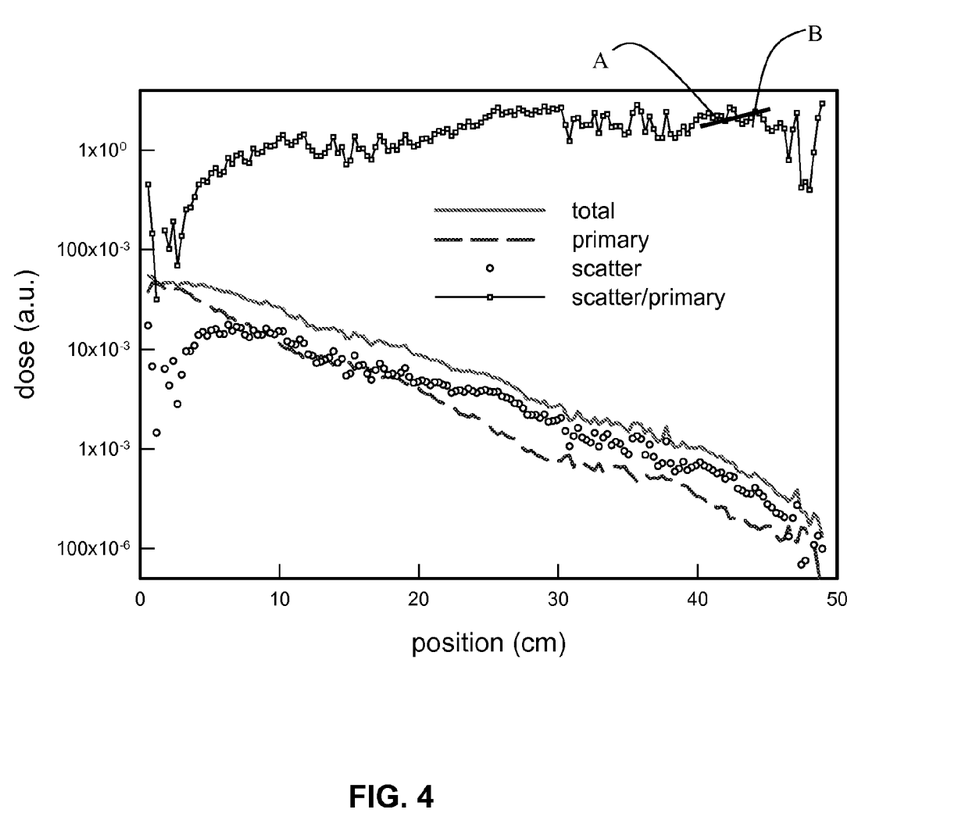
FIG. 4 is a diagram illustrating a primary-to-scatter ratio as a predictable quantity over a longitudinal distance through a medium of an object.

FIG. 4 illustrates a total dose of a cone beam inside an object (which may have an arbitrary geometry) with a known attenuation map. The primary and scattered doses may be separated from the total dose, for example, based on Equation (1).

In an example, if a detector is placed at a position A and another detector is placed at a position B, and if the attenuation properties of materials along the beam path between locations A and B are known, then based on Equation (1), the SPR can be derived. Using the readout of the total doses from point A and point B, separate primary and scatter doses can be derived based on the total doses and the SPR. This principle may be further illustrated in an example shown in FIG. 5.

Figure 5:
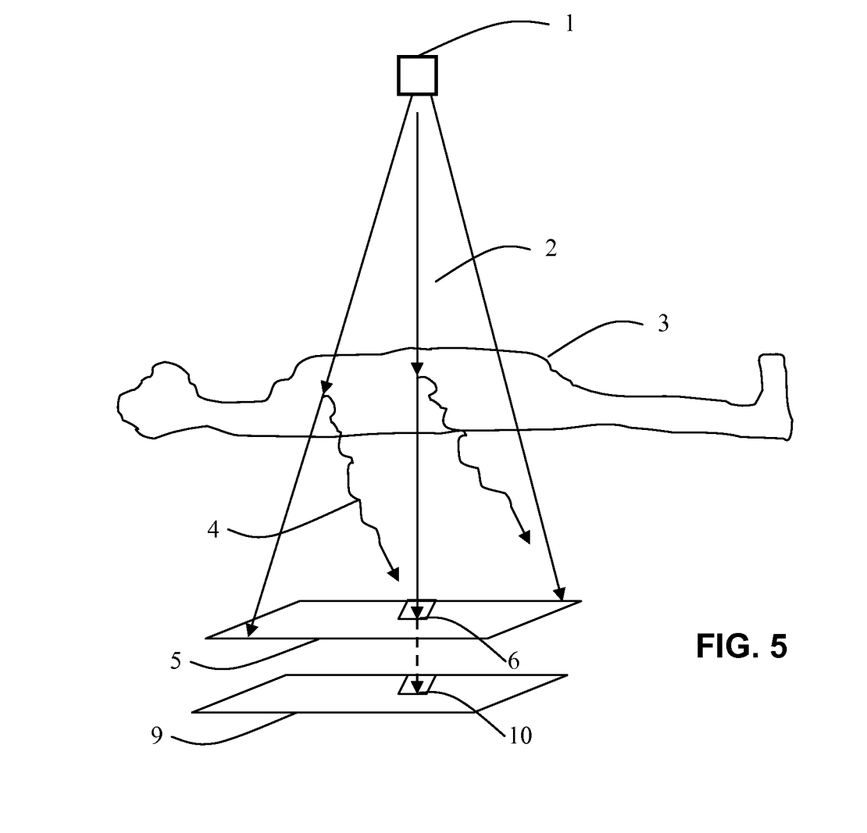
FIG. 5 is a schematic diagram illustrating an example configuration of using two layers of X-ray detectors for a same cone beam.

FIG. 5 illustrates, according to some implementations, that a flat-panel x-ray detector array 5 may be supplemented with a second detector array 9. The detector system according to the illustrated implementation includes two-layer detector arrays 5 and 9. The two array 5 and 9 may be flat panels, and may be separated by a known distance. One or more materials having known attenuation and scattering properties may fill a space between the two arrays.

The SPR, as a function of relative positions of detector element 6 and detector element 10, may be derived based on Monte Carlo simulations according to some implementations, or based on analytical solutions such as Equation (1) according to some implementations. The SPR may depend on the distance between the two layers, relative positions of detector elements, and the properties of the filling material(s). During a CT procedure, both layers may record different dosages at the substantially same time, and a primary dose may be derived based on the two dosages recorded by the two layers of detectors.

The filling material between the two layers may have measurable or known attenuation properties. Examples of such materials include, but are not limited to, air, water, plastic, solid water, rubber, etc.

According to some implementations, the effect of the two layers may alternatively be achieved using only one layer. This single layer may have its position moved along the beam direction, or against the beam direction, for example, from one exposure to another exposure. Such a recording of dose-distance relationship may allow the separation of primary and scatter using Monte Carlo simulations, or algorithms described in Equation (1) and alike. In some other implementations, the motion of the detector array may be replaced with, or supplemented by, moving the x-ray source 1.

In some other implementations, the detector arrays may alternatively be implemented using volumetric detector arrays, which may record a radiation dosage distribution in 3-D.

In some implementations, the individual detector elements in the two-layer detector array, or in the volumetric detector array, may be arranged such that they do not shadow each other in the beam. In some implementations, shadowing may be allowed, and algorithms may be implemented to take into account the shadowing based on the detectors' attenuation coefficients. The SPR can still be obtained in this approach.

In some implementations, the CT images reconstructed from a conventional CT method may be used as input to Monte Carlo simulations. The Monte Carlo simulations may track the photons and label them as primary or scattered photons. Through the Monte Carlo simulations, the fractions of primary and scattered components of the photons received by each detector may be determined, and a new set of images may be reconstructed using only the primary component. Iterations can be employed to obtain improved images.

In addition to obtaining a first set of images based on the primary radiation, a second set of images may also be obtained based on scattered radiations. This may be achieved, for example, by comparing the primary with the total radiations. The first set of images may contain the most accurate density/attenuation information of the internal structure of the object, and the second set of images may provide additional information that is also of diagnostic interests.

By separating the scattered component from the primary component according to implementations disclosed herein, the object density map may be generated with a much higher accuracy. This may be due to that, for example, the primary component may respond to the density variation in a more predictable way as compared with the scattered component, and the scattered component may tend to degrade the image quality. By reconstructing a patient attenuation coefficient map based on primary radiation only, the density of the patient's tissues may be quantitatively analyzed from the re-constructed CT image.

In some implementations, the mathematical approaches to separate primary and scattered radiations may be realized using computer algorithms. Such algorithms may be constructed based on the properties and behaviors of the primary and scatter components of x-ray radiations.

The properties and behaviors of the primary and scatter components of x-ray radiations may include, for example, that the primary component and the scattered component behave differently as the beam size increases. For example, as the beam size increases, the percentage of the primary component relative to the total dose may decrease.

In another example, at small fields (e.g., <0.5 cm in diameter), all the doses deposited in tissues may be mostly primary doses. Such a property may be used, according to some of the disclosed implementations and as demonstrated in the FIG. 2, to separate the primary component from the scattered component of an x-ray radiation. In an example, the x-ray radiation may be in an energy of about 140 keV, typical for the diagnostic imaging purposes.

In another example, the properties and behaviors of the primary and scatter components of x-ray radiations used to design algorithms according to some of the disclosed implementations may include that the primary component and the scattered component behave differently as the distance from the x-ray source increases. In the case of diagnostic x-ray, Equation (1) may be used to quantitatively represent one of such behaviors according to some of the implementations disclosed herein.

In yet another example, the primary component and the scattered component react differently to material (e.g., tissue) density variations when transporting through the material (e.g., tissue). Such different behaviors may be described (e.g., implicitly) in equations dominating Monte Carlo simulations of radiation transport. For example, each individual photon may be traced, and the primary and scattered components may be labeled within the Monte Carlo simulations. The final simulation results may be associated with the measured quantities.

Figure 6:
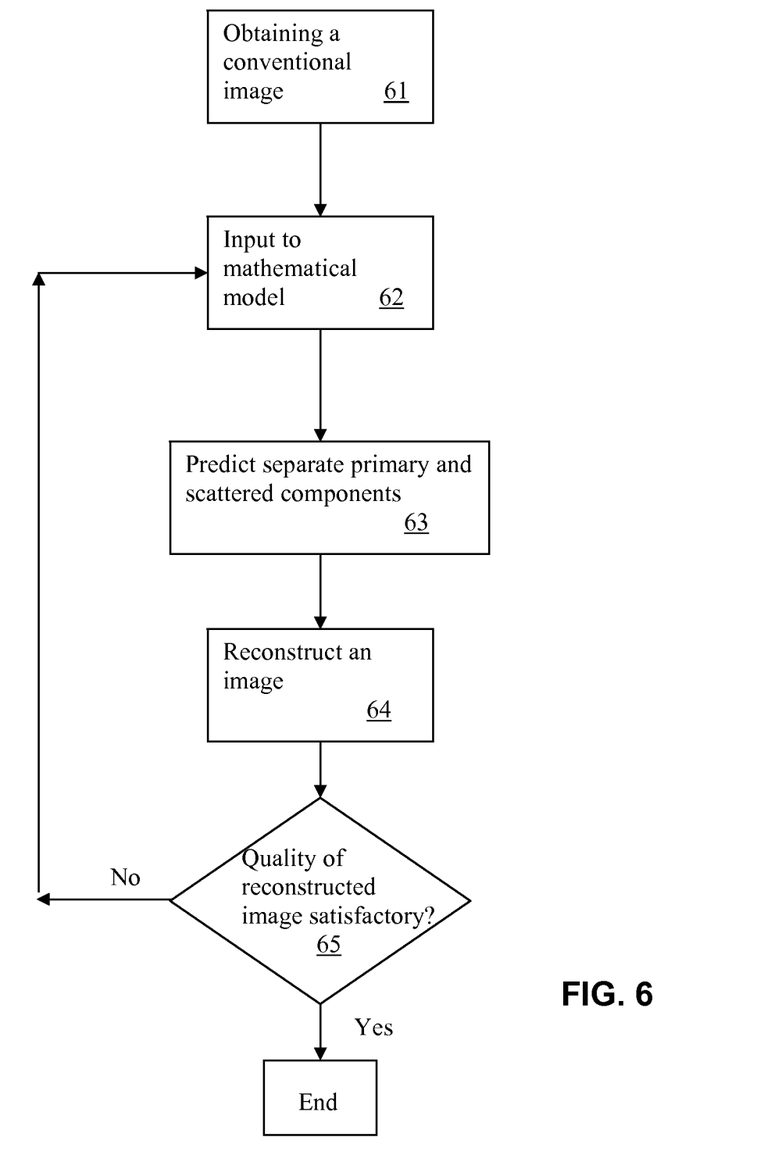
FIG. 6 is a flowchart illustrating an example method of improving an image quality by iterating image reconstruction using a primary component of radiation.

An example method of obtaining an improved CT image in accordance with some implementations is summarized in FIG. 6. An input image, such as a conventional image without separating the primary and scattered radiation components, may be first obtained in the step 61. The input image may be input to a mathematical model in the step 62. The mathematical model may include, for example, an analytical equation similar to Equation (1), and/or may include a Monte Carlo algorithm.

Using the mathematical model, a separation of primary and scattered radiation components may be realized in the step 63. An image may be subsequently reconstructed based on the primary radiation component in the step 64.

If the quality of the reconstructed image is deemed unsatisfactory in the step 65, the reconstructed image may be input to the mathematical model. Some of the steps may be iterated, for example, starting with the step 62.

If the quality of the reconstructed image is considered satisfactory, the reconstructed image may output for practical use. A separate image constructed based solely on the scattered radiation may optionally be generated, as the scattered radiation may also contain useful information.

Advantages of one or more embodiments disclosed herein may include, but are not limited to improved image quality with more accurate information of an internal structure based on primary radiation; optional images obtained from scattered radiations providing more useful information; achievable by incorporating algorithms into, or by replacing detector arrays of, existing imaging systems.

All references cited in the description are hereby incorporated by reference in their entirety. While the disclosure has been described with respect to a limited number of embodiments, those skilled in the art, having benefit of this disclosure, will appreciate that other embodiments can be advised and achieved which do not depart from the scope of the description as disclosed herein.

The invention claimed is:

1. A computed tomography (CT) imaging system configured to construct an image of an internal structure of an object, the imaging system comprising:
   a radiation source including a collimating or a blocking device configured to generate both a narrow beam and a wide beam of radiation;
   a detector configured to detect the radiation; and
   at least one processing circuit configured to:
      determine a scatter-to-primary ratio (SPR) of the wide beam based on the narrow beam;
      determine a primary component of the wide beam based on the SPR to thereby separate the primary component from a scattered component of the wide beam; and
      construct the image using the primary component.

2. The imaging system of claim 1, wherein the radiation source comprises a blocking device configured to generate both the narrow beam and the wide beam.

3. The imaging system of claim 1, wherein the detector is configured to move along a path of the narrow beam to thereby measure a radiation level at a plurality of positions along the path to facilitate the determining of the SPR.

4. The imaging system of claim 1, wherein the detector comprises a plurality of detection elements disposed at a plurality of positions along a path of the narrow beam to facilitate the determining of the SPR.

5. The imaging system of claim 1, further comprising a timing device configured to coordinate an emitting time from the radiation source and a detecting time of a detecting element of the detector, to thereby separate the primary component and the scattered component of the wide beam.

6. The imaging system of claim 1, wherein the at least one processing circuit is configured to use an analytical pencil beam model, and predict the primary component of the wide-beam X-ray radiation using the narrow beam based on the analytical pencil beam model.

7. The imaging system of claim 1, wherein the at least one processing circuit is configured to use a Monte Carlo algorithm, and predict the primary component of the wide-beam X-ray radiation.

8. The imaging system of claim 7, wherein the at least one processing circuit is configured to perform an iteration of an output image, wherein the output image is used as an input density map to the Monte Carlo algorithm, to generate more a accurate density map image.

9. The imaging system of claim 1, further comprising a timing device configured to turn on a detecting element for a short period such that the detecting element detects only the primary component.

10. The imaging system of claim 1, wherein the detector is configured to selectively read an output from a selected detecting element to thereby separate the primary and scattered components.

11. The imaging system of claim 1, wherein the at least one processing circuit is configured to generate an image of the internal structure based on the scattered component.

12. An image reconstruction method for Computed Tomography (CT), the method comprising:
determining a scatter-to-primary ratio (SPR) of a wide beam based on a narrow beam;
determining a primary component of the wide beam based on the SPR to thereby separate the primary component from a scattered component of the wide beam; and
constructing an image of an internal structure of an object using the primary component.

13. The method of claim 12, further comprising:
using a first set of CT images without separating the primary and scattered components as input density maps to a computer model;
constructing a second set of CT images based on the primary component using the computer model; and
iterating the above operations to obtain CT images with improved accuracy.

14. The method of claim 13, wherein the computer model comprises at least one of an analytical equation of an SPR as a function of a position and attenuation properties of a material along a beam path, or a Monte Carlo algorithm.

15. The method of claim 12, further comprising coordinating an emitting time from a radiation source and a detecting time of a detecting element, to facilitate separation of the primary component and the scattered component of the wide beam.

16. The method of claim 12, further comprising turning on a detecting element for a short period such that the detecting element detects substantially only the primary component.

17. The method of claim 12, further comprising selectively reading an output from a selected detecting element to thereby separate the primary and scattered components.

18. A non-transitory computer-readable medium having instructions stored thereon, the instructions comprising:
transmitting a narrow beam of radiation through an object onto a detector array;
transmitting a wide beam of radiation through the object onto the detector array;
recording radiation levels at a plurality of positions along a path of the narrow beam using the detector array;
calculating a scatter-to-primary ratio (SPR), using a computer model, as a function of position;
separating primary and scattered components of the wide beam based on the calculated SPR;
constructing a first set of CT images using the primary component; and
constructing a second set of CT images using the scattered component.

19. The non-transitory computer-readable medium of claim 18, wherein the computer model comprises an analytically-derived formula describing the SPR as a function of positions and attenuation properties of material along the path of the narrow beam.

20. The non-transitory computer-readable medium of claim 18, wherein the computer model comprises a Monte-Carlo-derived numerical relation describing the SPR as a function of positions and attenuation properties of material along the path of the narrow beam.

* * * * *